United States Patent [19]

Nanba et al.

[11] Patent Number: 5,236,567
[45] Date of Patent: Aug. 17, 1993

[54] ENZYME SENSOR

[75] Inventors: Akira Nanba, Shobara; Masahiro Fukaya, Aichi; Hajime Okumura, Handa; Yoshiya Kawamura, Konan, all of Japan

[73] Assignee: Nakano Vinegar Co., Ltd., Handa, Japan

[21] Appl. No.: 528,088

[22] Filed: May 24, 1990

[30] Foreign Application Priority Data

May 31, 1989 [JP] Japan .................. 1-135755
Dec. 5, 1989 [JP] Japan .................. 1-314310
Mar. 20, 1990 [JP] Japan .................. 2-68207

[51] Int. Cl.$^5$ .......................... G01N 27/26
[52] U.S. Cl. ..................... 204/403; 204/418; 435/817; 435/288; 435/291; 436/518; 436/806
[58] Field of Search ............ 204/403, 153.12, 416, 204/418, 419; 435/817, 288, 291; 436/518, 806

[56] References Cited

U.S. PATENT DOCUMENTS

| | | | |
|---|---|---|---|
| 4,224,125 | 9/1980 | Nakamura et al. | 204/153.12 |
| 4,490,464 | 12/1984 | Gorton et al. | 204/403 |
| 4,545,382 | 10/1985 | Higgins et al. | 204/403 |
| 4,704,193 | 11/1987 | Bowers et al. | 204/153.12 |
| 4,711,245 | 12/1987 | Higgins et al. | 204/403 |
| 4,897,173 | 1/1990 | Nankai et al. | 204/403 |

Primary Examiner—John Niebling
Assistant Examiner—Bruce F. Bell
Attorney, Agent, or Firm—Sherman and Shalloway

[57] ABSTRACT

An enzyme sensor, which comprises an enzyme-modified electrode and a counter electrode, wherein the enzyme-modified electrode comprises, as electrode components, an enzyme and/or an enzyme-containing substance and mediator. The enzyme sensor is useful in analysis, such as the analysis of compounds in foods or components in the living body, the diagnosis of diseases and the control of reaction processes. The preparation of the enzyme-modified electrode is also described.

4 Claims, 12 Drawing Sheets

A-A' CROSS SECTION

B-B' CROSS SECTION

ENZYME SENSOR

FIELD OF THE INVENTION

The present invention relates to an enzyme sensor used for measurement of several components in a solution. More particularly, the present invention relates to "Enzyme sensor, which comprises both an enzyme-modified electrode and a counter electrode, said enzyme-modified electrode comprising, as electrode components, an enzyme and/or an enzyme-containing substance and a mediator."

According to the present invention, an object component can be measured easily and rapidly. Hence, the present invention is not only useful as a measurement sensor in the areas of fermentation industry and chemical industry, but is also useful as a measurement sensor of several biological components in a sample from the living body, in the area of clinical tests, and can be used widely for diagnosis and examinations of several diseases, too.

BACKGROUND OF THE INVENTION

Enzyme sensor, in which the high specificity of an enzyme toward its substrate is used, is found to be useful for measurement of several compounds, and the enzyme sensor has already been practiced in quantitative analyses of glucose, etc. The enzyme sensor now practiced, in which an enzyme possessing high specificity toward a substance to be measured is immobilized, is used for determination of an object substance in a sample, by electrochemically detecting an amount of hydrogen peroxide formed, or of oxygen consumed when an enzyme acts on an object substance in a sample. Accordingly, enzymes to be employed in enzyme sensors of this type are restricted to oxidation enzymes, so-called "oxidases," which form hydrogen peroxide.

Usually, oxidases, which selectively oxidize substances to be measured, are separated from microorganisms selected through screening and are purified for use. However, a microorganism which produces an object enzyme is not always found through the screening process, and even if it is found, there are many cases where the microorganism cannot be employed owing to enzymatic properties, such as substrate specificity, the $K_m$ value, and stability. In addition, because of low productivity by microorganisms or difficult separation and purification, there are many cases where enzyme sensors do not come into practical use, and an enzyme sensor serving for practical use is only a glucose sensor under the present situation.

Concerning oxidase, an enzyme sensor is developed for measurement of ethanol by use of an alcohol oxidase originated in yeast, and its practical use is examined in the system of using a hydrogen peroxide electrode or an oxygen electrode, but actually, it does not bring about a commercial success. This is because substrate specificity of the enzyme is low and a life-time of the enzyme is considerably short.

On the other hand, as enzyme other than the oxidases above described, there are dehydrogenases which donate electrons occurring in the oxidation process to prosthetic groups, such as PQQ, FAD, NAD, and NADP, being not always accompanied by oxygen consumption nor hydrogen peroxide generation. In this type of enzymes, there are greater number of types than are oxidases. Of the dehydrogenases, the presence of enzymes suitable for sensor is also known.

Accordingly, the present inventors developed a new enzyme sensor with a substrate specificity higher than, and with a stability superior to, the sensor by means of enzyme originated in yeast in the preceding publication (Japanese Patent Application No. 253,850/87). The enzyme used in the sensor was an alcohol dehydrogenase having PQQ (pyrroloquinoline quinone) as a prosthetic group originated in acetic acid bacteria. By this invention, a sensor superior to the sensor by means of an enzyme originated in yeast was developed, resulting in one success.

However, dehydrogenases other than alcohol dehydrogenases have hardly been employed yet as a source of enzymes for the sensor. This is because the coenzymes, i.e. PQQ, FAD, NAD, and NADP, are of high prices, which leads to high analysis costs. In order to solve the problem, it was attempted, for example, to immobilize NAD and to regenerate for use, which does not come into practical use yet, though. On the other hand, a method employing an artificial electron acceptor as a mediator (an electron transport intermediate) is developed, thereby preparing an enzyme sensor for a high specificity toward glucose, etc., as well as toward ethanol, and its practical use is examined. However, it is evident that the cost is high even if an artificial mediator is employed, and mediators usually employed are usually coloring substances, so that the waste fluids are colored, to cause a problem of waste water treatments if discarded as it is. In addition, a high-priced mediator is wasted every measurement, thereby resulting in a further higher cost, so that the improvement has been desired.

It is proposed that an artificial mediator in the form of a thin film is applied to the surface of an electrode, which is then coated with an enzyme, followed by being further covered with a semipermeable membrane (EP 78636B1). In other methods, it was proposed that a mediator hardly soluble in water is incorporated into a electrode material (Agric. Biol. Chem., 52, 1557, (1988), and that in the case of a highly water-soluble mediator, first the mediator is added to an electrode, then a thin film is made of a mixture comprising an ionic high molecular compound and an enzyme, so as not to elute the mediator into an electrolyte (Agric, Biol. Chem., 52, 3187 (1988)). However, in both of the cases, it is troublesome to prepare the electrodes, and the enzyme is employed so as to form a thin film, after the incorporation of mediator. In the latter case, there is no examination of employment of dehydrogenase.

As earlier described, conventional enzyme-modified electrodes have several problems; the preparation is troublesome; very difficult operations are required for mass-production of quality-controlled product; in addition, their life-time for repeating use is short; and enzymes that can be utilized are limited. Accordingly, instead of the conventional troublesome process of successive covering of the thin membrane layer of a mediator, the thin membrane layer of enzyme, and the layer of a semipermeable membrane with the surface of an electrode, the present inventors made an electrode material with a homogeneous composition from electron carriers, such as graphite carbon pastes, which are usually employed as an electrode material, an enzyme, and a mediator, by the addition of suitable vehicles like liquid paraffin, by mixing them to a homogeneous composition thereby the surface of an electrode substrate (e.g.

carbon electrode) being covered with the electrode material (referred to as an enzyme-modified electrode material), and by this considerably easy method, the present inventors established a process of the preparation of an enzyme-modified electrode for respective enzymes, to complete the present invention after several researches for the purpose of providing the enzyme-modified electrode-incorporated sensor excellent in properties.

SUMMARY OF THE INVENTION

The present invention provides an enzyme sensor which comprises an enzyme-modified electrode and a counter electrode, wherein the enzyme-modified electrode comprises, an enzyme and/or an enzyme-containing substance and a mediator. The enzyme-modified electrode is a further aspect of the invention.

The enzyme-containing substance may, for example, be selected from the group consisting of cells, a cultured medium and disrupted cells of a microorganism producing said enzyme, and fractionation components, cellular extracts, cell membrane fraction and a crude enzyme from said disrupted microorganism cells. The enzyme is suitably a dehydrogenase, for example, alcohol dehydrogenase, aldehyde dehydrogenase, glucose dehydrogenase, fructose dehydrogenase, sorbitol dehydrogenase, or glycerol dehydrogenase.

The term mediator, as used herein, refers to a substance which can mediate in the transfer of electrons, such as a redox compound and/or a coenzyme. Suitable examples include p-benzoquinose, ferrocene, dimethylferrocene, potassium ferricyanide, phenazine methosulphate, 2,6-dichlorophenol indophenol, PQQ, FAD, NAD, and NADP. Particularly suitable combinations of enzyme and mediator include the following pairs: aldehyde dehydrogenase and p-benzoquinone; fructose dehydrogenase and dimethylferrocene; sorbitol dehydrogenase and dimethylferrocene; and glycerol dehydrogenase and potassium ferricyanide.

The electrode components contain carbon or graphite.

The present invention further provide a method for preparing an enzyme-modified electrode which comprises preparing, an enzyme-modified electrode material by dissolving a water-insoluble mediator in an organic solvent, adding liquid paraffin thereto, followed by removing the solvent and mixing the resultant mixture with graphite powder and an enzyme and/or an enzyme-containing substance, and applying the resulting material to the surface of a carbon electrode.

The enzyme-modified electrode may also be prepared by mixing reversed micells, into which a water-soluble mediator is incorporated, with graphite powder and an enzyme and/or an enzyme-containing substance, to yield an enzyme-modified electrode material which is then applied to the surface of a carbon electrode.

The enzyme-modified electrode material which can be used for the preparation of the enzyme-modified electrode of the invention may also be prepared by mixing a water-insoluble complex of a ferricyanide compound and a cationic surface active agent with liquid paraffin and then with graphite powder and an enzyme and/or enzyme-containing substance.

The invention further provides measuring equipment, which comprises a reaction chamber, a constant voltage power supply part, a current voltage converting part, and an amplifier part, said reaction chamber being equipped with a sample injection port, an electrolyte inlet, a waste liquid outlet, a stirring device, a counter electrode, and an enzyme-modified electrode of the invention.

The present invention has provided a novel enzyme-modified electrode prepared by an extremely easy method, and a novel enzyme sensor which comprises combining said enzyme-modified electrode and a counter electrode, wherein the enzyme-modified electrode is formed in the state of an enzyme and a mediator being uniformly mixed together with other electrode components, and the enzyme sensor shows a little change in electrode components caused by elution of the mediator, etc., as well as shows stable property, in repeating uses. The enzyme sensor according to the present invention is excellent in responsibility and reproductibility of measured values, and since the present invention can employ a wide variety of enzymes, selection of an enzyme according to its substrate specificity for use makes various component measurements possible. In particular, there is a great advantage in the employment of dehydrogenases which have hardly been employed as a sensor enzyme.

According to the present invention, a mediator, together with enzyme, is firmly immobilized to an electrode, so that a mediator or enzyme of high price is not eluted, and the mediator can be used for long time for repeating uses and thus a great economical effect can be achieved. In addition, since colored mediators employed in many cases are not eluted, so that colorination of waste liquids is prevented, resulting in a significant effect, i.e., elimination of the problem for waste liquid treatment.

Therefore, by use of the present invention, a very small amount of a compound in foods or a component in the living body can be measured rapidly and correctly, and it can also be used in diagnosis of diseases, control of fermentation process, and control of a reaction process.

BRIEF DESCRIPTION OF THE FIGURES

In FIGS. 1, 2A and 2B, the numerals indicate as follows:

1 . . . enzyme-modified electrode
2 . . . graphite electrode
3 . . . conductive adhesive
4 . . . copper screw
5 . . . nut (double)
6 . . . Ag/AgCl$_2$ electrode
7 . . . sample injection port
8 . . . magnetic stirrer
9 . . . stirrer
10 . . . reaction chamber
11 . . . pump
12 . . . electrolyte
13 . . . waste liquid
PS . . . constant-voltage power source CV-A . . . current-voltage conversion and amplifier
A/D . . . A/D conversion
RE . . . recorder
CP . . . computer

DETAILED DESCRIPTION OF THE INVENTION

Enzymes employed in the present invention may be any of ones if they can catalyze a oxidation-redox reaction of substances to be measured and can transfer electrons originated in the reaction. For example, dehydrogenases having coenzymes, such as PQQ, FAD, NAD, and NADP, are preferably used.

More particularly, the following dehydrogenases are preferably used; for ethanol measurement, alcohol dehydrogenases originated in Acetobacter aceti IFO 3284, Gluconobacter suboxydans IFO 12528, Acetobacter altoacetigenes FERM BP-491; for measurement, of acetaldehyde, aldehyde dehydrogenases originated in the three bacteria above described; for glucose measurement, glucose dehydrogenases originated in Gluconobacter suboxydans IFO 12528 and Gluconobacter suboxydans IFO 3254; for fructose measurement, fructose dehydrogenase originated in Gluconobacter industrius IFO 3260; for sorbitol measurement, sorbitol dehydrogenase originated in Gluconobacter suboxydans IFO 3254; for glycerol measurement, glycerol dehydrogenase originated in Gluconobacter industrius IFO 3260.

In addition, sucrose can be measured with an enzyme sensor having an electrode comprising, as its components, an enzyme which degrades sucrose to produce glucose or fructose, such as invertase originated in baker's yeast or Candida utilis, together with glucose dehydrogenase or fructose dehydrogenase.

Among enzymes utilized in the present invention, particularly preferable enzymes can include ones which are accumulated in the state of being bound to the cell membranes of microorganisms when cultured (referred to as a membrane-bound enzyme, hereinafter). The membrane-bound enzymes are superior in stability when mixed as an electrode component, the enzyme is hardly eluted when the electrode is used, good reproducible measured values are given, and there is also an advantage in that they are available with low prices as an enzyme source.

In the present invention, enzyme-containing substances as well as enzymes above described can widely be used. The enzyme-containing substance is suitably selected from the group consisting of fractionation components, extracts, cell-membrane fractions, membrane-bound enzymes, and crude enzymes from said enzyme-producing microorganisms, said enzyme-producing microorganisms culture said disrupted microorganisms. If purified enzyme is desired, microorganism is disrupted by a common method, such as sonication or French pressure, followed by ammonium sulfate fractionation or fractionation by means of several types of chromatography, to separate and purify an object enzyme. In the case of employment of a membrane-bound enzyme, as shown above, good results can be given even if the disrupted microorganism is employed without the enzyme being highly purified.

The mediators used in the present invention are not particularly restricted, if they can transfer electrons occurring in the enzyme reaction, but mediators used are preferred to be selected so as to proceed in transferring the electrons smoothly. In addition, it is also possible to employ two or more mediators simultaneously. Specifically, artificial mediators, such as p-benzoquinone, ferrocene, dimethylferrocene, potassium ferricyanide, 2,6-dichlorophenol indophenol, can preferably be employed singly or in combination, but original enzyme's prosthetic groups, such as PQQ, FAD, NAD, and NADP can also be employed.

The electrode components utilized in the present invention comprises an enzyme and a mediator as essential components. However, any one other than these components can be employed, if it is an electron carrier capable of constituting the electrode. As such an electron carrier, usually carbon or graphite is preferably employed.

The preparation of an enzyme-modified electrode comprising both an enzyme and a mediator as electrode components can be carried out, e.g., according to the following method.

For employment of a water-insoluble mediator, such as p-benzoquinone, ferrocene, and dimethylferrocene, first the mediator is dissolved in a solvent like ether, etc. and the solution is added to a suitable amount of liquid paraffin and mixed well. After removing the solvent by a common method, such as by use of reduced pressure, the remaining product is mixed with an enzyme and graphite powder.

The adopted ratio of liquid paraffin to graphite powder to enzyme is generally (1-3):(0.5-1.5):1, and a minimum enzyme activity is 0.5 to 1 unit of alcohol dehydrogenase activity per 1 mg of protein.

In place of liquid paraffin, a hydrophobic or water-insoluble substance which is liquid at room temperature, such as hydrocarbons having 10 or more carbon atoms can be used.

For employment of a water-soluble mediator, such as potassium ferricyanide, phenazine methosulphate, and 2,6-dichlorophenol indophenol, a mediator-containing reversed micells are formed with a surface active agent, in order for the mediator to be incorporated into an electrode material, and mixed with an enzyme and graphite powder, to prepare an enzyme-modified electrode material containing mediator.

Also, in the case of potassium ferricyanide, a water-insoluble complex can be prepared by mixing a cationic surface-active agent therewith. The resultant complex was added to liquid paraffin in a suitable ratio, well mixed, and then mixed with an enzyme and graphite powder, so that an enzyme-modified electrode comprising a mediator can be prepared. The cationic surface-active agent which may be preferably used in the step includes dimethyl di-n-octadecyl ammonium bromide, trioctyl methyl ammonium chloride, cetyl pyridinium chloride, dodecyl pyridinium chloride, tetradecyl dimethylbenzyl ammonium chloride, etc.

The mixing ratio of a mediator-containing liquid paraffin or potassium ferricyanide—a cationic surface-active agent to graphite powder to enzyme is preferably employed in the range of (1-3):(0.5-1.5):1.

Any other than graphite powder, liquid paraffin, or a surface active agent can also be employed if it is an electrode material capable of being mixed with the enzyme.

As described above, various types of compounds, such as prosthetic groups, redox compounds (e.g., quinone, methylene blue, etc.) and the like can suitably be employed as mediators.

Figure 1:
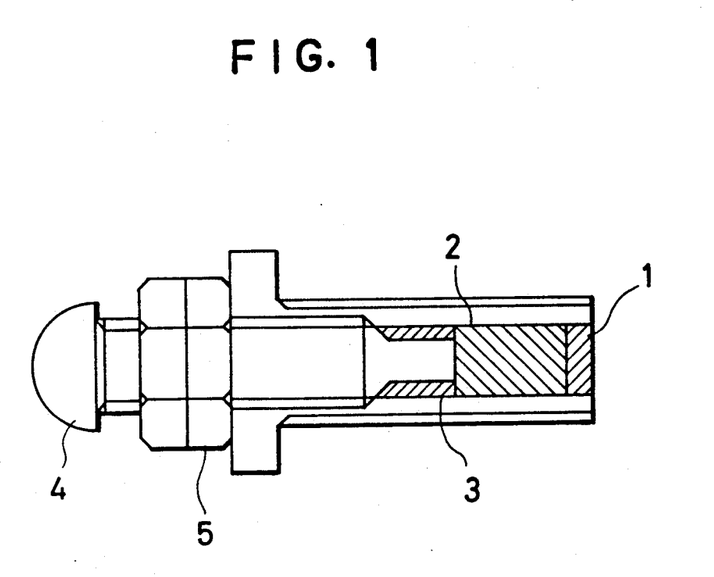
FIG. 1 the structure of an enzyme-modified electrode.

FIG. 1 shows the illustrated example of an enzyme-modified carbon electrode relating to the present invention. In the example, the mixture, in which graphite powder and a mediator are mixed well in an appropriate proportion, is uniformly mixed with an enzyme, and the resulting mixture is applied to the surface of an electrode, to prepare the enzyme-modified carbon electrode.

The amount of an enzyme electrode material to be applied is not particularly restricted if the electrode can respond to a substance to be measured. However, from a viewpoint of workability, a response speed, and an economical factor, it is preferably applied in the range of 0.3 to 2 mg per 1 mm$^2$ of the electrode surface or 50 to 500 μm in thickness.

Figure 2A:
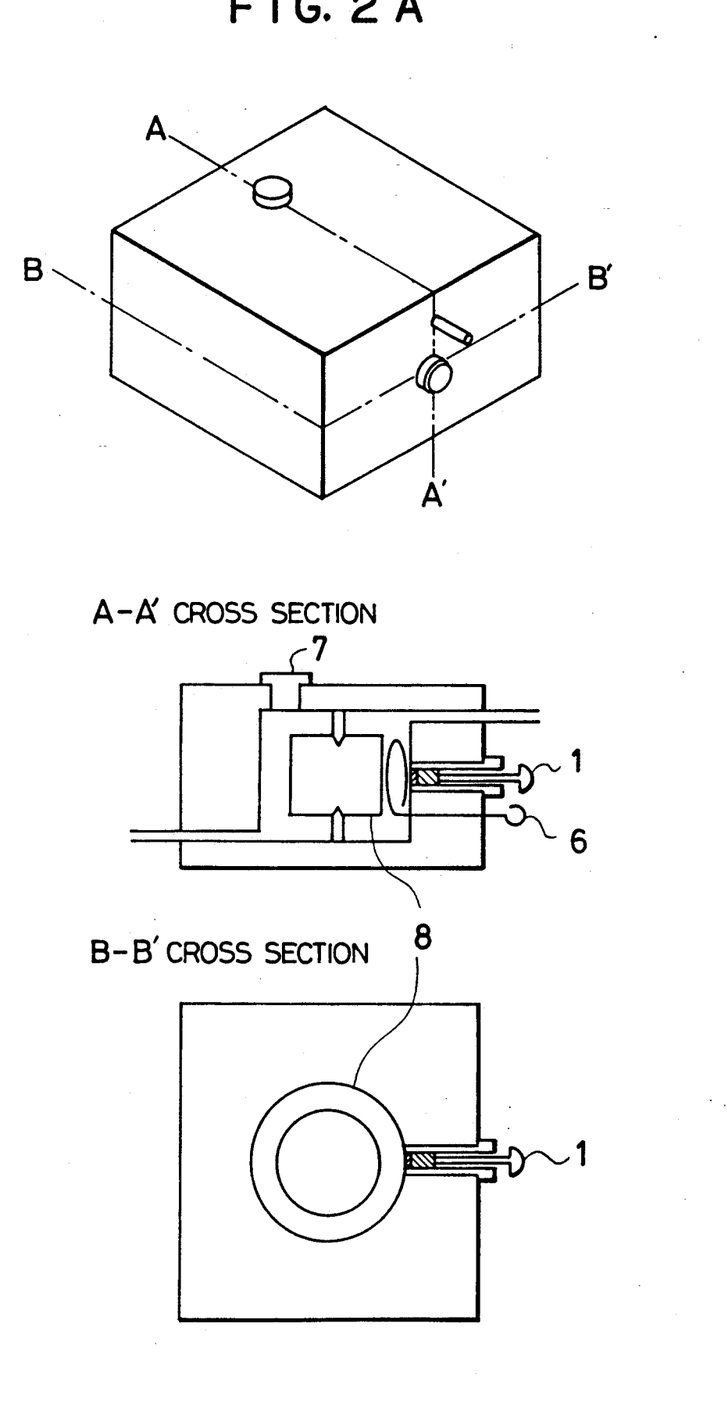
FIG. 2A shows the structure of reaction chamber and FIG. 2B shows a measuring apparatus.
Figure 2B:
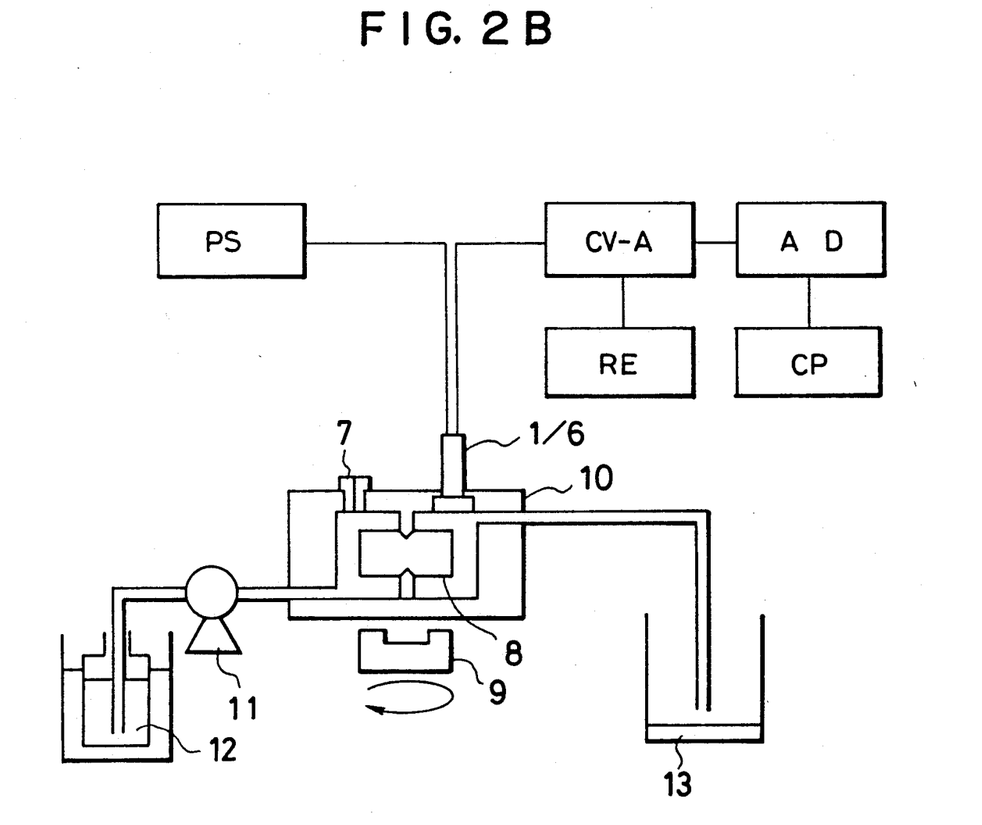
Figure 3A:
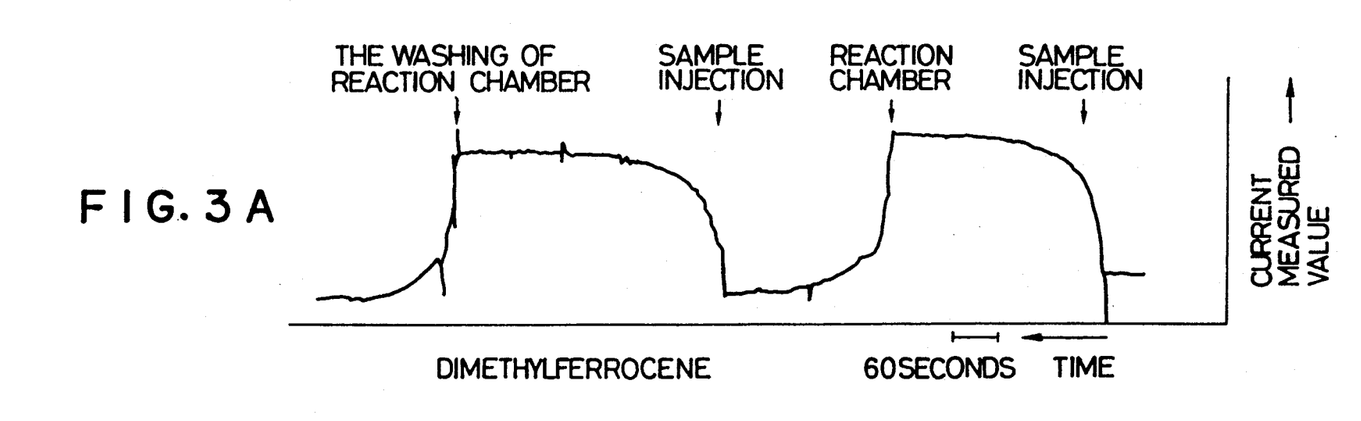
FIG. 3A, 3B, 3C, and 3D show the response curve to a 10% ethanol solution in the case where four kinds of mediator were used.
Figure 3B:
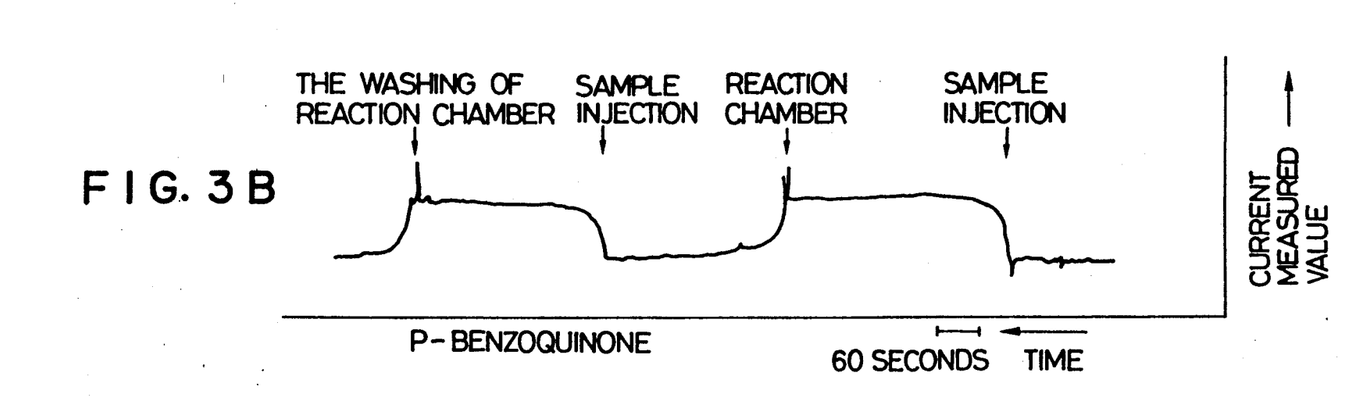
Figure 3C:
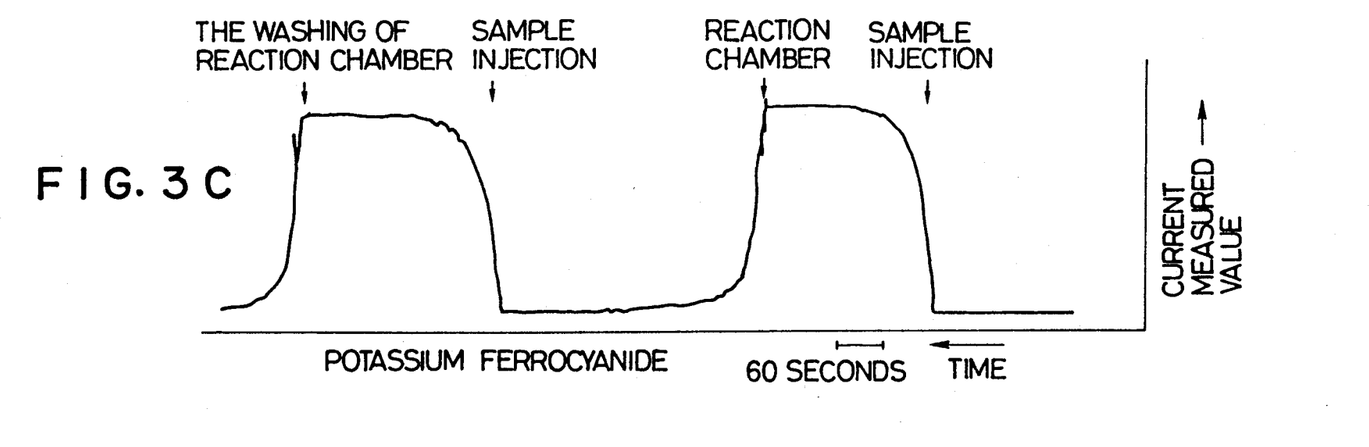
Figure 3D:
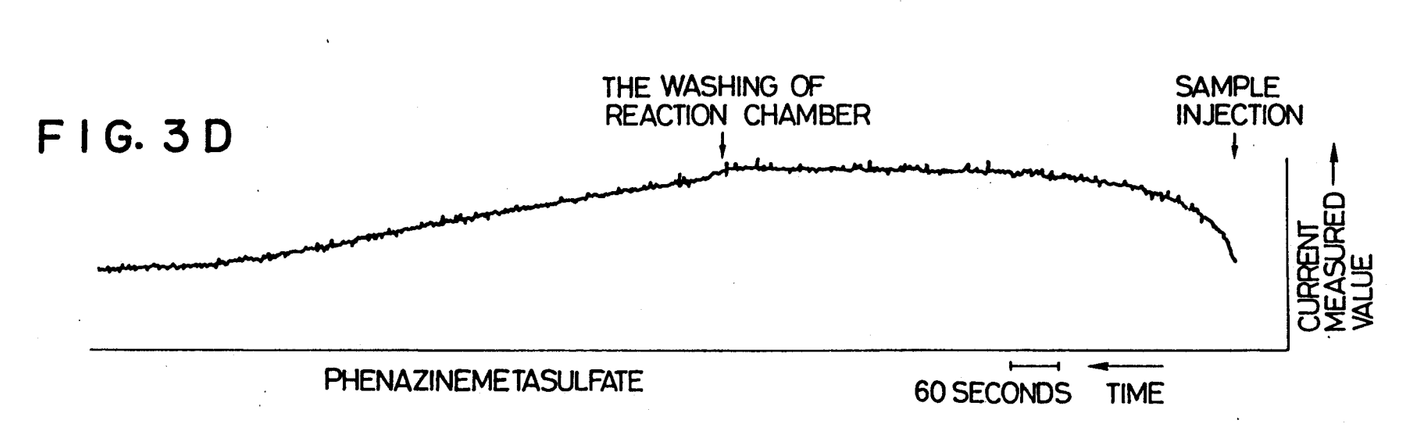

The electrode thus prepared is attached to an apparatus shown in FIG. 2, and an object substance in a sample solution is measured. That is, first, a reaction chamber is set up as shown in FIG. 2A. In the middle of the reaction chamber, a sample chamber or an electrolytic cell is made, and a stirring equipment like magnetic stirrer, etc. is provided therewith. The sample chamber is equipped with an enzyme-modified electrode (FIG. 1) and a counter electrode (e.g., Ag/AgCl$_2$ electrode), together with a sample inlet, an electrolyte inlet, and a waste fluid drain, and thus the assembly of the reaction chamber is finished.

Using the reaction chamber thus set up, measurements are carried out with an apparatus illustrated in FIG. 2B.

That is, an enzyme-modified carbon electrode illustrated in FIG. 1 is attached to the sample chamber (electrolytic cell), and the sample chamber is filled with electrolyte by use of a pump, to which a voltage is applied while a suitable counter electrode being used. Then, a sample containing a measured substances is injected in an appropriate amount through a sample injection port. The current value of oxidation current occurring by the reaction of a measured substance included in a sample with the enzyme in the enzyme-modified carbon electrode is recorded with a recorder after being converted to a voltage value with a current-voltage converting circuit, or is measured with a computer by sending the current to the computer after the A/D conversion. By comparing an observed oxidation current of a sample with those of standard solutions of predetermined concentrations, a substance to be measured which the sample contains can be determined. In this case, the surface area, in contact with a liquid to be measured, of the enzyme-modified electrode according to the present invention may generally be as small as about 3 mm$^2$. The measurements can be carried out at temperatures of 10° to 40° C. and in the range of pH 4 to 8.

The present apparatus can be used as a flow-injection type apparatus by continuous feeding of an electrolyte during measurement. By using an apparatus of the flow-injection type, it is possible to extend the range of concentrations to be measured.

The present invention is explained more detail, referring to the examples below.

It is only shown in the examples below that precipitates obtained by ultracentrifugation of the disrupted cells of dehydrogenase-producing bacteria are used as enzyme. However, the present invention is not restricted to the examples described below, and suitably purified enzyme can be employed, or enzyme can be selected for use, according to the type of a substance to be measured.

EXAMPLE 1

Preparation of a Cell Membrane-Bound Alcohol Dehydrogenase and a Cell Membrane-Bound Aldehyde Dehydrogenase A cultivated both of Acetobacter altoacetigenes FERM BP-491 was centrifuged and collected, and the obtained bacterial cells were disrupted with a French pressure. After the disrupted cells were subjected to ultra centrifugation (100,000 g, 60 min. 4° C.), precipitates were employed as a cell membrane-bound alcohol dehydrogenase and as a cell membrane-bound aldehyde dehydrogenase.

EXAMPLE 2

Preparation of a Cell Membrane-Bound Glucose Dehydrogenase and a Cell Membrane-Bound Sorbitol Dehydrogenase A cultivated broth of Gluconobacter IFO 3254 was treated in the same manner as in Example 1 above described, and the obtained precipitates were employed as a membrane-bound glucose dehydrogenase and a membrane-bound sorbitol dehydrogenase.

EXAMPLE 3

Preparation of a Membrane-Bound Alcohol Dehydrogenase-Modified Carbon Electrode Comprising a Water-Insoluble Mediator 1 g of dimethylferrocene was dissolved in 1 ml of ether, 1 ml of liquid paraffin was added and mixed well, and the ether was removed by evaporation under reduced pressure. With the mixture were mixed graphite powder of not greater than 250 mesh size and the enzyme prepared in Example 1 above described in the ratio of 3:3:1 (ratio by weight) and the mixture was subjected to dehydration treatment for 3 hrs. under reduced pressure, to prepare an enzyme-modified electrode material.

The electrode material prepared was applied to the surface of a carbon electrode part contacting liquid as shown in FIG. 1 in a small amount, to prepare a membrane-bound alcohol dehydrogenase-modified carbon electrode comprising dimethylferrocene.

A membrane-bound alcohol dehydrogenase-modified carbon electrode comprising p-benzoquinone was prepared in the same manner as the above-described method except that p-benzoquinone is employed.

EXAMPLE 4

Preparation of a Membrane-Bound Alcohol Dehydrogenase-Modified Carbon Electrode Comprising a Water-Soluble Mediator To 1 ml of α-bromonapthalene was added 0.025 g of Aerosol OT, and the mixture was dispersed well. Aqueous solution of 0.1 ml of 1 M potassium ferricyanide was added to the resultant dispersion and was then subjected to sonication for 20 min, while sometimes being shaken. The water remaining in the upper part was absorbed into a filter paper for removement. In this manner, α-bromonaphthalene containing reversed micells into which potassium ferricyanide was incorporated was prepared. Separately, α-bromonaphthalene, graphite powder of not greater than 250 mesh size, and the enzyme prepared in Example 1 described above were mixed in the ratio of 3:3:1, respectively, and the mixture was treated for dehydration under reduced pressure.

To the resultant mixture was added the above α-bromonaphthalene containing the reversed micells in the ratio of 1:2 and mixed well, to prepare an enzyme-modified electrode material.

Using the electrode material thus prepared, a membrane-bound alcohol dehydrogenase-modified carbon electrode comprising potassium ferricyanide was prepared in the same manner as in Example 3 described above.

A membrane-bound alcohol dehydrogenase-modified carbon electrode comprising phenazine methosulphate was prepared in the same manner as in the above-described method except that the mediator is phenazine methosulphate in place of potassium ferricyanide.

EXAMPLE 5

Preparation of a Membrane Bound-Glucose Dehydrogenase-Modified Carbon Electrode Comprising a Water-Soluble Mediator Using the enzyme prepared in Example 2 described above, a membrane-bound glucose dehydrogenase-modified carbon electrode comprising potassium ferricyanide was prepared in the same manner as in Example 4 described above.

EXAMPLE 6

Measurement of Ethanol Concentration

The enzyme-modified carbon electrode comprising the mediator prepared in Example 3 or 4 previously described was attached to the apparatus shown in FIG. 2, and the reaction chamber was filled with an electrolyte which was prepared by degassing 0.1 M phosphate buffer containing 0.1 M KCl (pH 6.0) under reduced pressure by use of a pump, and a magnet in the reaction chamber was stirred with a stirrer. A constant voltage of +0.6 V was applied to a silver/silver chloride electrode as another electrode in the reaction chamber, and the current value was recorded with a recorder. The reaction chamber was kept at 20° C.

5 μl of the sample containing 10% (W/V) ethanol was injected from a sample injection port by use of a microsyringe, and the current value obtained under the above-described reaction conditions was measured, to obtained the response curve as shown in FIG. 3.

Even if any of the mediator was employed, by injection of a ethanol-containing sample, the oxidation current was increased and finally turned constant. In a sample not containing ethanol, no oxidation current increase was observed.

Figure 4:
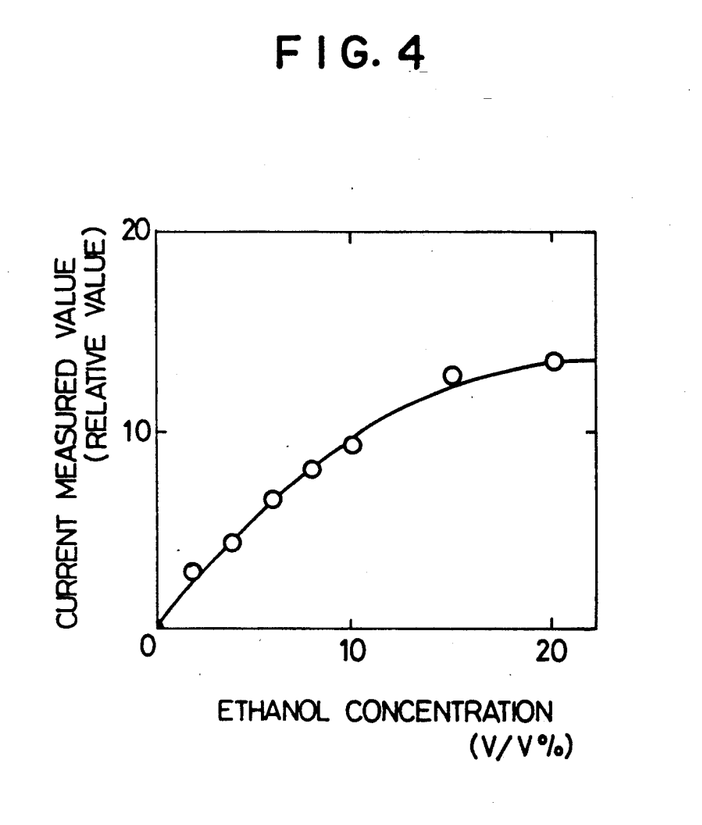
FIG. 4, FIG. 5, FIG. 6, FIG. 7, FIG. 8, FIG. 9, and FIG. 10 show one example of a calibration curve for measurement of ethanol, glucose, aldehydes, fructose, sorbitol, glycerol, or sucrose, respectively, using the enzyme sensors according to the present invention.

When the respective mediators were employed, the oxidation currents, converted into their voltage values are as follows: 14 mV in case dimethyl ferrocene was employed, 5 mV in case p-benzoquinone was employed, 44 mV in case potassium ferricyanide was employed, 8 mV in case phenazine methosulphate was employed. Using the enzyme electrode comprising potassium ferricyanide by which the highest current value could be obtained, the effect of ethanol concentration was examined. As a result, data as shown in FIG. 4 were obtained where the current measured values increased in response to the ethanol concentration. In addition, in order to investigate the electrode stability, the standard deviation of the current values obtained were 1.9% in the case where the same sample (ethanol concentration; 10%) was examined successively 13 times, which showed the reproductibility to be considerably high.

EXAMPLE 7

Measurement of Glucose Concentration

Figure 5:
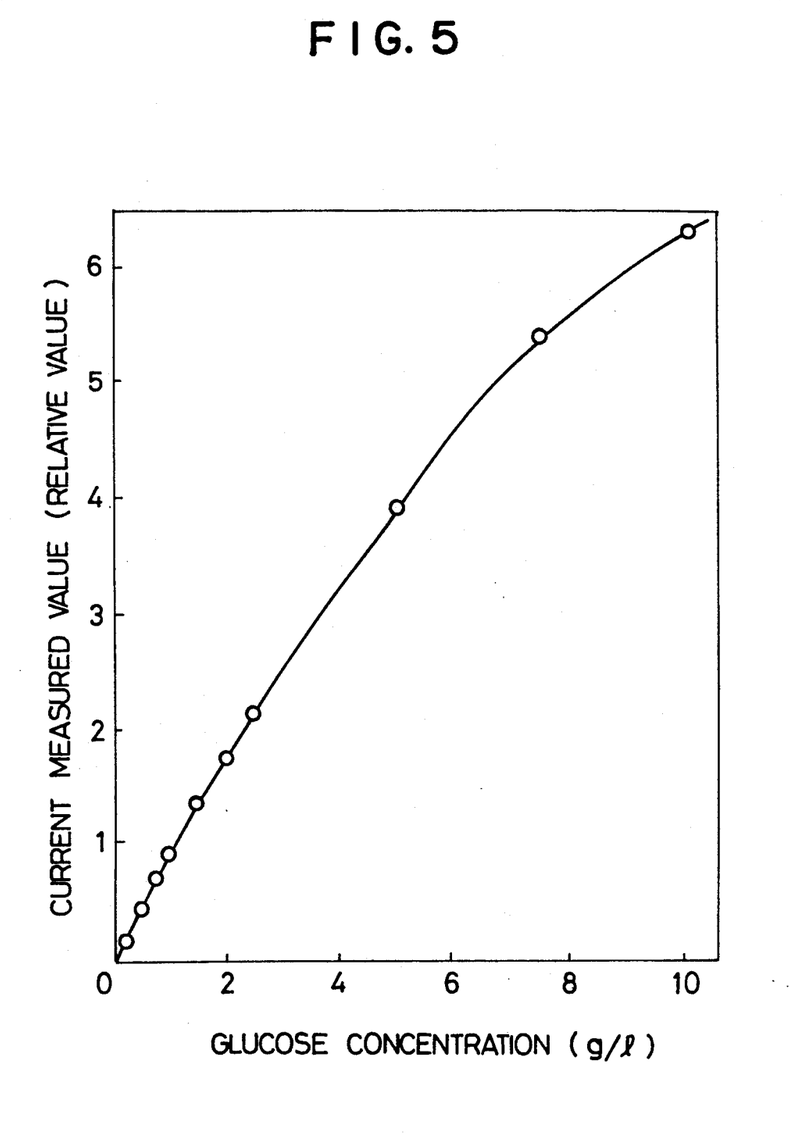

The enzyme-modified carbon electrode comprising the mediator prepared in Example 5 above described was attached to an apparatus shown in FIG. 2, and under the same conditions as in Example 6 as above described, each 5 μl of a sample containing glucose of various concentrations was injected through the sample injection port by use of a microsyringe, and current values obtained were recorded with a recorder. By plotting the relationship between the current values and the glucose concentrations, the result shown in FIG. 5 was obtained, and the measured values increased in response to the glucose concentrations in the samples were obtained.

EXAMPLE 8

Preparation of a Membrane-Bound Fructose Dehydrogenase and a Membrane-Bound Glycerol Dehydrogenase A cultured broth of Gluconobacter industrius IFO 3260 was treated in the same manner as in Example 1 above described. The resultant precipitates were employed as a membrane-bound fructose dehydrogenase and as a membrane-bound glycerol dehydrogenase.

EXAMPLE 9

Preparation of a Membrane-Bound Aldehyde Dehydrogenase-Modified Carbon Electrode Comprising a Water-Insoluble Mediator 1 g of p-benzoquinone was dissolved in 1 ml of ether, and 1 ml of liquid paraffin was added thereto, followed by being mixed well, and the solvent was removed by evaporation under reduced pressure. To this mixture were mixed graphite powder not larger than 250 mesh size and the enzyme standard prepared in Example 1 above described were mixed in the ratio of 1:1:1 (ratio by weight). The mixture was then subjected to a dehydration under reduced pressure for 1 hr., to prepare an enzyme-modified electrode material. Using the enzyme-modified electrode material prepared, a membrane-bound aldehyde dehydrogenase-modified carbon electrode comprising p-benzoquinone was prepared in the same manner as in Example 3 above described.

EXAMPLE 10

Preparation of a Membrane-Bound Fructose Dehydrogenase Modified Carbon Electrode Comprising a Water-Insoluble Mediator Using the enzyme prepared in Example 8 above described, a membrane-bound fructose dehydrogenase-modified carbon electrode comprising dimethyl ferrocene was prepared in the same manner as in Example 3 above described.

EXAMPLE 11

Preparation of a Membrane-Bound Sorbitol Dehydrogenase-Modified Carbon Electrode Comprising a Water-Insoluble Mediator Using the enzyme prepared in Example 2 above described, a membrane-bound sorbitol dehydrogenase-modified carbon electrode comprising dimethyl ferrocene was prepared in the same manner as in Example 3 above described.

EXAMPLE 12

Preparation of a Membrane-Bound Glycerol Dehydrogenase-Modified Carbon Electrode Comprising a Water-Soluble Mediator Using the enzyme prepared in Example 8 above described, a membrane-bound glycerol dehydrogenase-modified carbon electrode comprising potassium ferricyanide was prepared in the same manner as in Example 4 above described.

EXAMPLE 13

Measurement of Acetaldehyde and N-Hexaldehyde Concentrations

Figure 6:
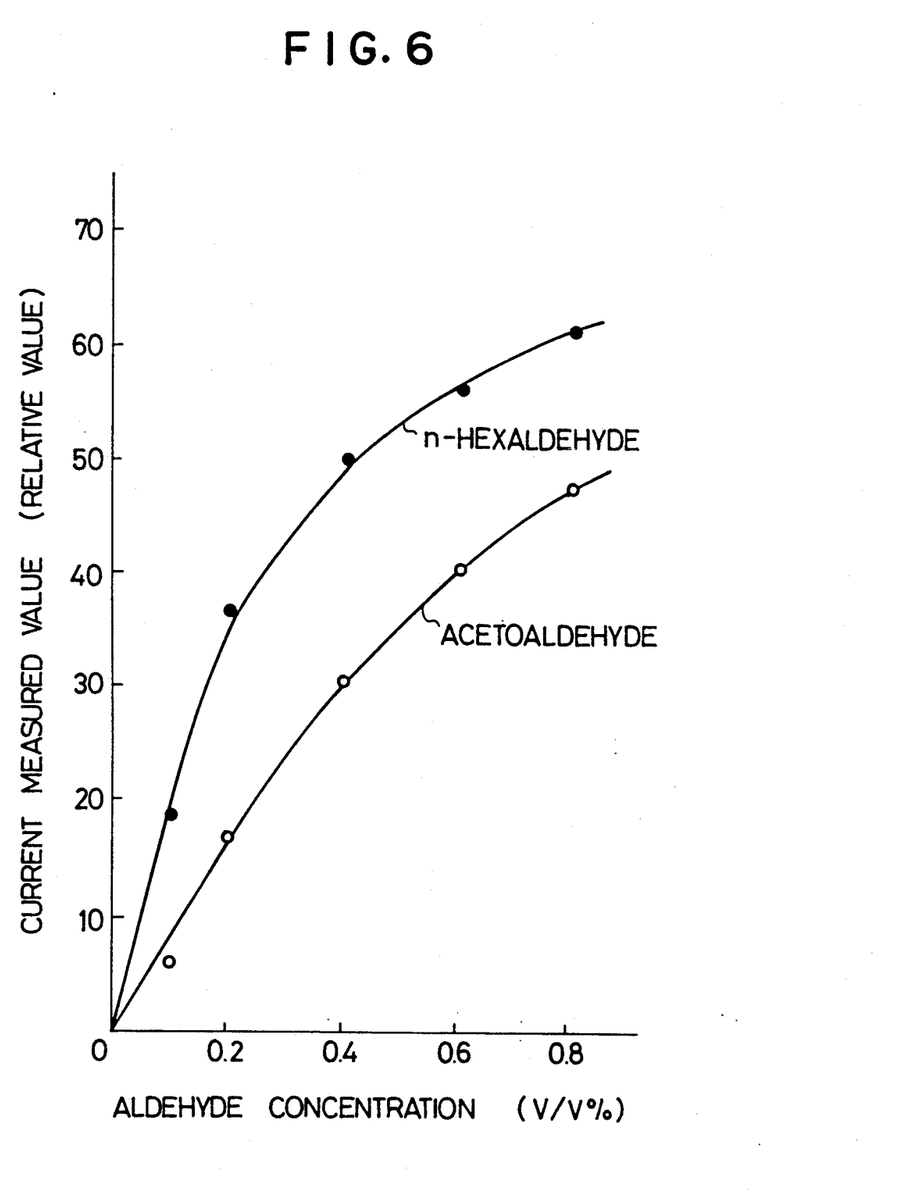

The enzyme modified-carbon electrode comprising the mediator prepared in Example 9 above described was fixed in an apparatus shown in FIG. 2, and under the same measuring conditions as in Example 6 above described, each 10 μl of samples containing acetaldehyde or n-hexaldehyde of various concentrations was injected from a sample injection port by means of a microsyringe. After sample injection, current value change for 2 min. was recorded with a recorder. By plotting the relationship between the current values being constant after 2 min. and the concentrations of acetaldehyde or n-hexaldehyde in samples, the result shown in FIG. 6 was obtained, so that the measured values increased in response to the aldehyde concentrations in samples could be obtained.

EXAMPLE 14

Measurement of Fructose Concentration

Figure 7:
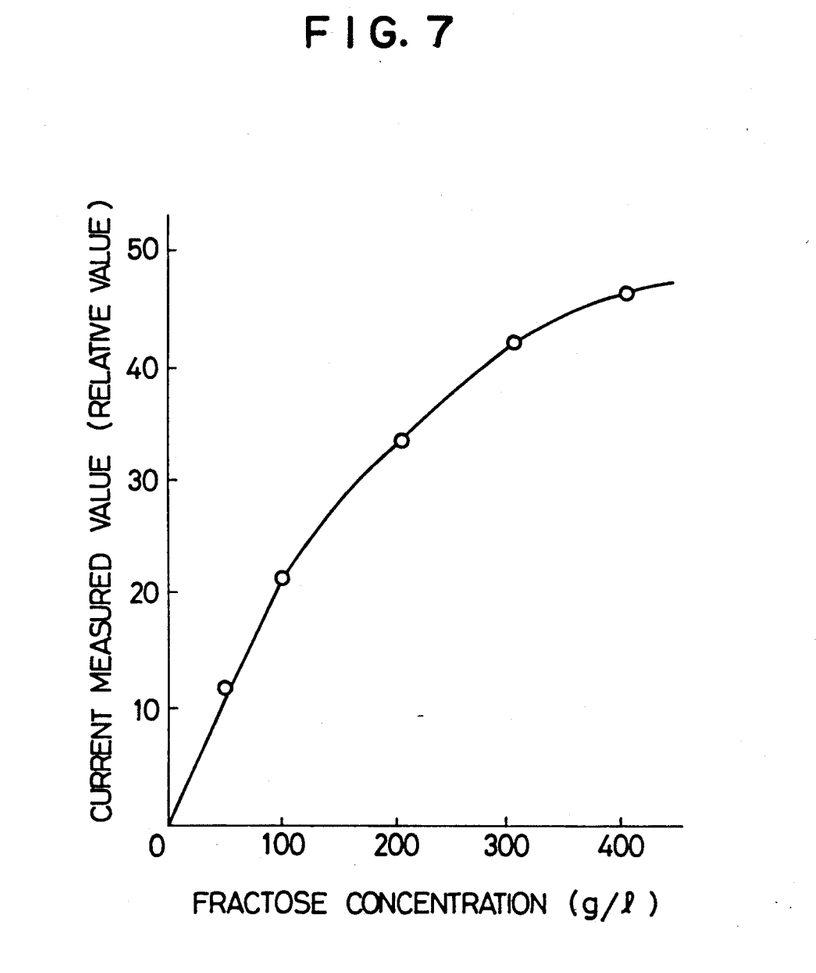

The enzyme-modified carbon electrode comprising the mediator prepared in 10 above described was attached to an apparatus shown in FIG. 2, and under the same measuring conditions as in Example 6 above described, each 10 μl of a sample containing fructose of various concentrations was injected from the sample injection port by use of a microsyringe. Following sample injection, current values after 2 min. were recorded with a recorder. By plotting the relationship between the current values and the fructose concentrations, the current values corresponding to the fructose concentrations in samples were measured, as shown in FIG. 7.

EXAMPLE 15

Measurement of Sorbitol Concentration

Figure 8:
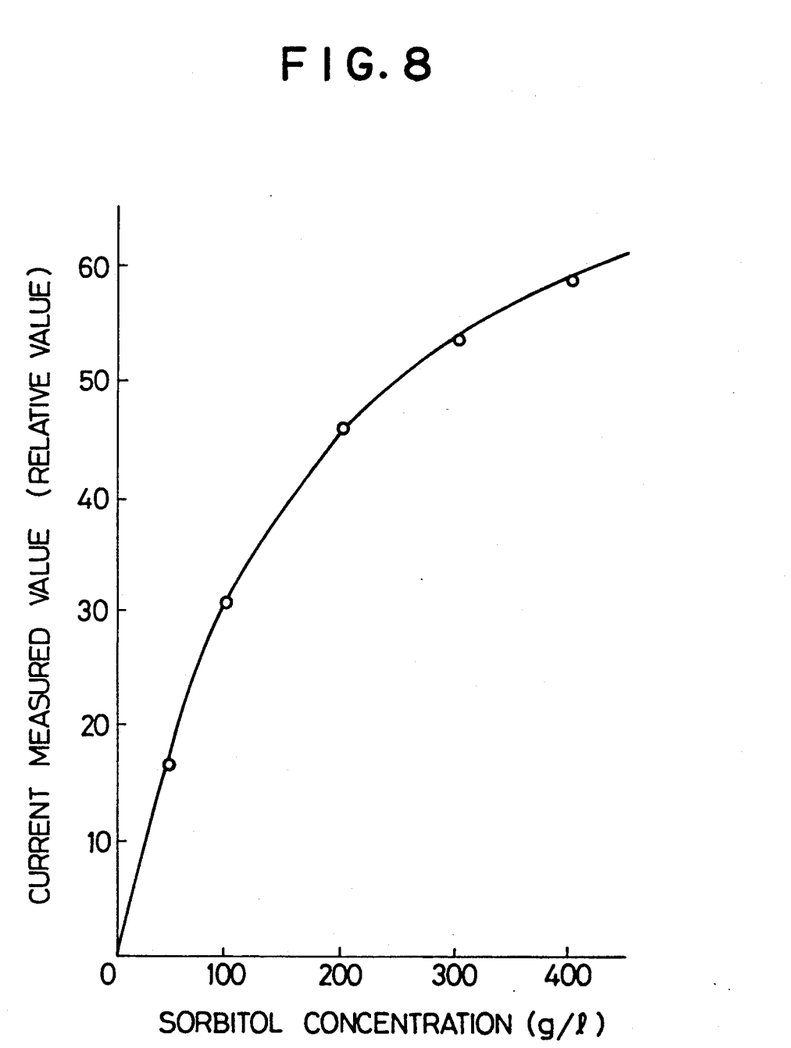

The enzyme-modified carbon electrode comprising the mediator prepared in Example 11 above described was attached to an apparatus shown in FIG. 2, and measurements were carried out under the same measuring conditions as in Example 6 above described. 10 μl of a sample containing sorbitol of various concentrations was injected from the sample injection port by use of a microsyringe. The change of current values was recorded with a recorder. By plotting values based on the current change for 2 min. after the injection and the sorbitol concentrations in samples, the measured values, as shown in FIG. 8, were correlated with the sorbitol concentrations.

EXAMPLE 16

Measurement of Glycerol Concentration

Figure 9:
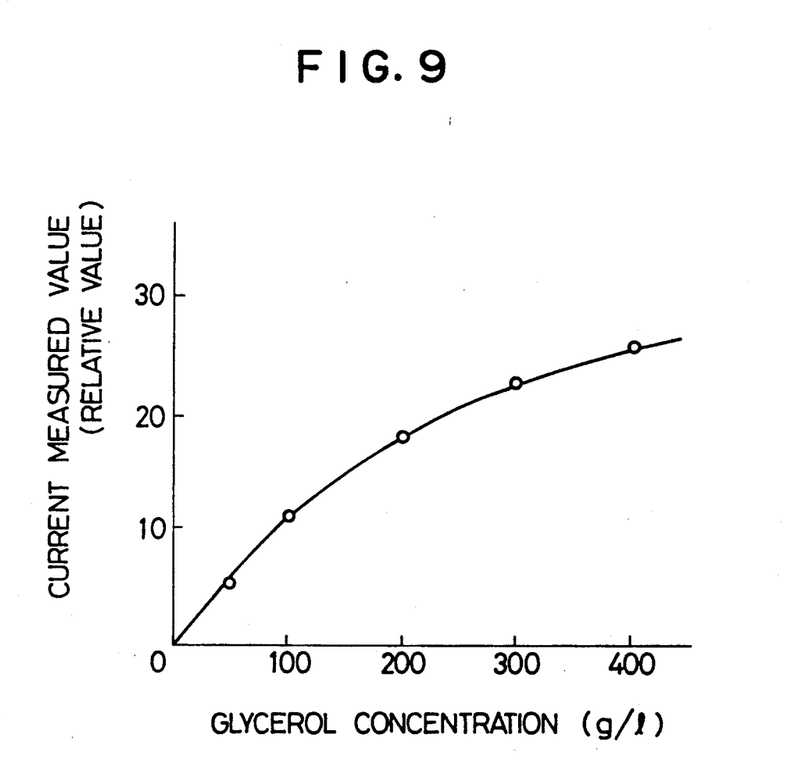

Using the enzyme-modified carbon electrode comprising the mediator prepared in Example 12 above described, the relationship between the glycerol concentrations and the measured current values was determined in the same manner as in Example 15 above described. Results show, as shown in FIG. 9, that the glycerol concentrations and the measured current values were correlated.

EXAMPLE 17

Preparation of a Membrane-Bound Glucose Dehydrogenase—Invertase-Modified Carbon Electrode Comprising a Water-Insoluble Mediator The enzyme prepared in Example 2 above described was mixed with invertase (from Sigma, Ltd., baker's yeast origin, 400 units/mg) in the ratio of 2:1. Using the resultant enzyme mixture containing membrane-bound glucose dehydrogenase and invertase, a membrane-bound glucose dehydrogenase—invertase modified-carbon electrode comprising p-benzoquinone was prepared in the same manner as in Example 9 above described.

EXAMPLE 18

Measuring of Sucrose Concentration

Figure 10:
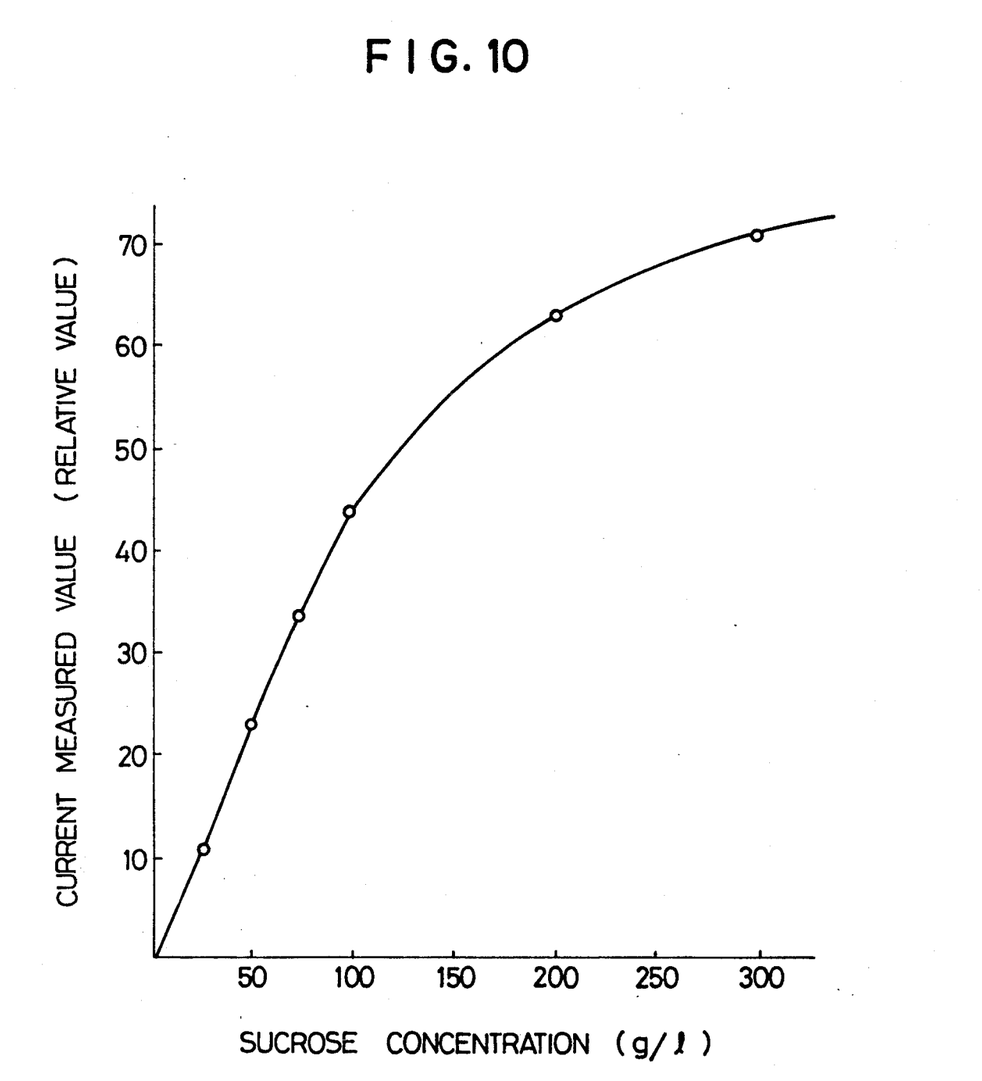

Using the enzyme-modified carbon electrode comprising the mediator prepared in Example 17 as above described, the relationship between the sucrose concentrations and the measured current values was determined in the same manner as in Example 15 above described except that an injection sample amount is 5 μl. Results showed, as shown in FIG. 10, that the sucrose concentrations and the measured current values were correlated.

EXAMPLE 19

Preparation of a Complex of Potassium Ferricyanide and a Cationic Surface-Active Agent 100 ml of 10 mM aqueous solution of dimethyl di-n-octadecyl ammonium bromide and 10 ml of 30 mM aqueous solution of potassium ferricyanide were prepared. The both solutions were combined, and mixed well by stirring for 30 min. The formed solids were separated by centrifugation (6,000×g, 10 min.) and obtained as precipitates. The precipitates were well washed twice with water. The obtained precipitates were allowed to stand one whole day at room temperature and dried enough, to obtain a complex of water-insoluble potassium ferricyanide—dimethyl di-n-octadecyl ammonium bromide (500 mg).

EXAMPLE 20

Preparation of a Cell Membrane-Bound Alcohol Dehydrogenase-Modified Carbon Electrode Comprising the Complex of Potassium Ferricyanide—Dimethyl Di-N-Octadecyl Ammonium Bromide 80 mg of the complex of potassium ferricyanide—dimethyl di-n-octadecyl ammonium bromide prepared in Example 19 above described was mixed well with 1 g of liquid paraffin. To 25 mg of the mixture were added 10 mg of the enzyme standard prepared in 1 above described and 10 mg of graphite powder not larger than 250 mesh size, and homogeneously mixed, to prepare an enzyme-modified electrode material. A small amount of the electrode material prepared was applied to a part of the surface of the electrode shown in FIG. 1, said part of the surface being to come into contact with a liquid. Thus, a cell membrane-bound alcohol dehydrogenase-modified carbon electrode comprising the complex of potassium ferricyanide—dimethyl di-n-octadecyl ammonium bromide was prepared.

EXAMPLE 21

Measurement of Ethanol Concentration

Using the enzyme-modified carbon electrode comprising the mediator prepared in 20 above described, the relationship of the ethanol concentrations in a sample and the measured values of current was determined in the same manner as in Example 6 above described. As shown in FIG. 11, the ethanol concentrations and the measured values of current were correlated.

EXAMPLE 22

Preparation of a Cell Membrane-Bound Alcohol Dehydrogenase-Modified Carbon Electrode Comprising a Complex of Potassium Ferricyanide—Cetyl Pyridinium Chloride and Measurement of Ethanol Concentration Cetyl pyridinium chloride was used in place of dimethyl di-n-octadecyl ammonium bromide in Example 19 above described, and a complex of potassium ferricyanide—cetyl pyridinium chloride was obtained according to the same method as in Example 19 above described. Using the resultant complex, an enzyme-modified electrode material was prepared in the same manner as in 20 above described. A small amount of the electrode material prepared was applied to a part of the surface of the electrode shown in FIG. 1, said part of the surface being to come into contact with a liquid, whereby a cell-bound alcohol dehydrogenase-modified carbon electrode comprising the complex of potassium ferricyanide—cetyl pyridinium chloride was prepared. Using the prepared enzyme-modified carbon electrode comprising the mediator, the relationship between the ethanol concentrations and the measured values of current was determined in the same manner as in Example 6 above described. As shown in FIG. 12, the ethanol concentrations and the measured values of current were correlated.

We claim:

1. An enzyme sensor which comprises an enzyme-modified electrode and a counter electrode, wherein the enzyme-modified electrode comprises, as electrode components, a combination of (i) an enzyme or an enzyme-containing substance or an enzyme and an enzyme-containing substance and (ii) a mediator, wherein the enzyme and mediator are, respectively: aldehyde dehydrogenase and p-benzoquinone; fructose dehydrogenase and dimethylferrocene; sorbitol dehydrogenase and dimethyl ferrocene; glycerol dehydrogenase and potassium ferricyanide; or alcohol dehydrogenase and a complex of potassium ferricyanide and a cationic surface-active agent.

2. A sensor according to claim 1, wherein the enzyme-containing substance is selected from the group consisting of cells of a microorganism producing said enzyme, a culture medium and disrupted cells of a microorganism producing said enzyme, fractionation components of disrupted cells of a microorganism producing said enzyme, cellular extracts of disrupted cells of a microorganism producing said enzyme, cell membrane fraction of disrupted cells of a microorganism producing said enzyme and a crude enzyme from disrupted cells of a microorganism producing said enzyme.

3. A sensor according to any one of claims 1 and 2, wherein the electrode components contain carbon or graphite.

4. A measuring apparatus which comprises a reaction chamber, a constant voltage power supply part, a current voltage converting part, and an amplifier part, said reaction chamber being equipped with a sample injection port, an electrolyte inlet, a waste liquid outlet, a stirring device, a counter electrode, and an enzyme-modified electrode, wherein said enzyme-modified electrode comprises, as electrode components, (i) an enzyme or an enzyme-containing substance or an enzyme and an enzyme-containing substance and (iii) a mediator.

* * * * *